US006846955B2

(12) United States Patent
Hof et al.

(10) Patent No.: US 6,846,955 B2
(45) Date of Patent: Jan. 25, 2005

(54) PROCESS FOR RACEMISING AN ENANTIOMER-ENRICHED SCHIFF BASE OF AN AMINO ACID AMIDE

(75) Inventors: Robert Patrick Hof, Panningen (NL); Petrus Johannes Hermsen, Nijmegen (NL); Ronus de Bode, Bosch en Duin (NL)

(73) Assignee: DSM N.V., Heerlen (NL)

( * ) Notice: Subject to any disclaimer, the term of this patent is extended or adjusted under 35 U.S.C. 154(b) by 465 days.

(21) Appl. No.: 09/887,933

(22) Filed: Jun. 22, 2001

(65) Prior Publication Data

US 2001/0056209 A1 Dec. 27, 2001

(30) Foreign Application Priority Data

Jun. 22, 2000 (NL) ............................................ 1015495

(51) Int. Cl.[7] ...................... C07C 231/16; C07C 233/05
(52) U.S. Cl. ...................... 564/160; 564/164; 564/165; 564/198
(58) Field of Search ................. 564/160, 164, 564/165, 198

(56) References Cited

U.S. PATENT DOCUMENTS

| 4,172,846 A | 10/1979 | Boesten | ...................... 260/558 |
| 4,847,412 A | * 7/1989 | Boesten et al. | ............. 564/164 |
| 5,679,857 A | * 10/1997 | Hijiya et al. | ................ 564/304 |

FOREIGN PATENT DOCUMENTS

EP 716062 6/1996

OTHER PUBLICATIONS

Database WPI Section Ch, week 198607 Derwent Publications Ltd., London, GB; AN 1986–046542 XP002160541 & JP 61 001652 A (Nissan Chem Ind Ltd.), Jan. 7, 1986.

* cited by examiner

*Primary Examiner*—Shailendra Kumar
(74) *Attorney, Agent, or Firm*—Morrison & Foerster LLP

(57) ABSTRACT

The invention relates to a process for racemising an enantiomer-enriched Schiff base of a primary amino acid amide with a strong base that is chemically reactive towards water. The reaction is conducted in an organic solvent. Preferably a metal alkoxide, a metal alkyl, a metal amide, or a metal hydride, in particular a metal alkoxide is applied as the strong base. As the Schiff base preferably N-benzylidene primary amino acid amide is used, with the primary amino acid amide preferably being derived from an aliphatic primary amino acid amide, for example tertiary-leucine amide. As organic solvent use is preferably made of an aromatic hydrocarbon, a cyclic, aliphatic hydrocarbon or a ether, in particular an aromatic hydrocarbon is applied. The invention may also be applied for the racemisation of an enantiomer-enriched primary amino acid amide.

11 Claims, No Drawings

PROCESS FOR RACEMISING AN ENANTIOMER-ENRICHED SCHIFF BASE OF AN AMINO ACID AMIDE

The invention relates to a process for racemising an enantiomer-enriched Schiff base of a primary amino acid amide with a strong base in an organic solvent, Such racemisation of enantiomer-enriched Schiff bases of primary amino acid amides is known from U.S. Pat. No. 4,847,412. The process described therein, however, employs bases from the groups of alkali or alkaline-earth metal hydroxides and tetraalkylammonium hydroxides and a water-miscible organic solvent. In many cases this reaction fails to proceed or proceeds only slowly.

The invention provides a process for the racemisation of primary amino acid amides that does not have the above-mentioned drawbacks. This is achieved according to the invention by the strong base used being a base that is chemically reactive towards water.

Application of the process according to the invention allows enantiomer-enriched Schiff bases of primary amino acid amides to be racemised efficiently and with a strongly reduced likelihood of byproducts being formed.

In the scope of the invention primary amino acid amides are understood to be amino acid amides of which the amide-$NH_2$ is unsubstituted. Particularly also Schiff bases of aliphatic primary amino acid amides, which cannot be racemised or can be racemised only very slowly by the process according to U.S. Pat. No. 4,847,412, may be racemised relatively quickly via the method according to the invention. Aliphatic primary amino acid amides are here understood to be primary amino acid amides in which the p-carbon atom does not form part of an aromatic ring structure. Examples of aliphatic primary amino acid amides are tertiary-leucine amide, phenylalanine amide, methionine amide, aminobutyric acid amide, valine amide, leucine amide, isoleucine amide and allysine amide acetal.

EP-A-716062 discloses the preparation of a D-amino acid-N-(S)-α-alkylbenzylamide from the corresponding L-amino acid-N-(S)-α-alkylbenzylamide, in which a racemisation reaction occurs.

The enantiomer-enriched Schiff bases of primary amino acid amides that are used as a starting compound in the process according to the invention often are obtained as byproducts of enantiomeric cleavage reactions of chiral compounds wherein the other enantiomer is aimed at. Racemisation of the unwanted enantiomer according to the invention enables the yield of the desired enantiomer to be strongly increased.

"Racemisation" is understood to be the lowering of the e.e. of enantiomer-enriched compounds preferably to 0–80%, in particular to 0–30%.

In the process according to the invention a strong base is applied that is chemically reactive towards water. A "strong base" is understood to be a base with a $pK_b$ lower than for example 7 at 25° C. Examples of such bases are given in L. Kolditz (Hrsg.), Anorganikum Teil 1, 9. Aufl., VEB Deutscher Verlag der Wissenschaften, Berlin, 1981, p. 455–459. "Chemically reactive towards water" here means that water is deprotonated, with formation of a hydroxide, on coming into contact with such a base. As a strong base preferably a metal alkoxide is used, for example potassium tertiary-butoxide, sodium ethoxide or sodium methoxide, a metal alkyl, for example butyllithium or methyllithium, a metal amide, for example sodium amide or lithium diisopropylamide or a metal hydride, for example sodium hydride or potassium hydride.

The quantity of strong base to be applied is not critical. The strong base may be applied in a catalytic amount. Preferably 0.1–1000 mole % of the strong base relative to the amide is applied. In particular 1–100 mole % of the strong base relative to the amide is applied. If part of the base loses its reactivity due to the presence of protic contaminants, this may be corrected, if necessary, by adjusting the quantity of the base.

As organic solvent use is preferably made of a substituted or unsubstituted aromatic hydrocarbon, a cyclic aliphatic hydrocarbon or an ether, in particular an aromatic hydrocarbon. Examples of such organic solvents are toluene, chlorobenzene, anisole, cyclohexane, methylcyclohexane and tetrahydrofuran.

The temperature at which the racemisation takes place is preferably 20–200° C. The racemisation reaction will proceed relatively slowly at low temperatures, while at higher temperatures secondary reactions are more likely. As a rule, the best results are obtained when racemisation is conducted at 50–150° C.

If desired, the obtained mixture of enantiomers of the Schiff base of the primary amino acid amide may subsequently be converted into the mixture of enantiomers of the corresponding primary amino acid amide. Preferably this conversion is carded out in the presence of an acid or through reduction with hydrogen and a palladium catalyst.

An inorganic acid, for example sulphuric acid or hydrochloric acid, may suitably be applied as the acid. The temperature during the acid hydrolysis prefably is 0–80° C. After addition of water, the primary amino acid amide may be recovered from the aqueous layer of the reaction mixture for example by adding a strong base, for example potassium hydroxide, in which process the formed potassium salt precipitates, whereupon the mixture of enantiomers may be isolated from the amino acid amide by means of traditional techniques, for example by evaporating the solvent. The reaction mixture may also be applied as such in a resolution.

The process according to the invention may also especially suitably be applied in the racemisation of an enantiomer-enriched primary amino acid amide In that case the enantiomer-enriched primary amino acid amide is first converted into an enantiomer-enriched Schiff base, which is then racemised according to the invention and the obtained mixture of enantiomers of the Schiff base of the primary amino acid amide is converted into a mixture of enantiomers of the primary amino acid amide. The enantiomer-enriched primary amino acid amide may be converted into the enantiomer-enriched Schiff base of the primary amino acid amide by reaction with an aldehyde or a ketone. Such conversion may be conducted for example in the manner described in U.S. Pat. No. 4,172,846. Preferably a benzaldehyde is used. The benzaldehyde may be unsubstituted or may be substituted with for example a hydroxyl group, nitro group, halogen, alkyl group with 1–6 C atoms, alkoxy group with 1–6 C atoms and a hydroxyalkyl group with 1–6 C atoms.

The invention is elucidated with reference to the following examples.

EXAMPLE I

N-Benzylidene-R-tertiary-leucine amide (5.4 g, 24.8 mmol, e.e. 95.6%) and potassium-tertiary-butoxide (KOtBu, 0.6 g, 4.96 mmol) were suspended in 50 ml of tetrahydrofuran. The mixture was heated to reflux. Samples were analysed by chiral HPLC after 1.5 (e.e. 66.0%) and 4 hours (e.e. 37.2%).

EXAMPLE II

N-Benzylidene-R-tertiary-leucine amide (5.4 g, 24.8 mmol, ee 95.6%) and KOtBu (0.6 g, 4.96 mmol) were suspended in 50 ml of cyclohexane. The mixture was heated to reflux. Samples were analysed by chiral HPLC after 2 (e.e. 52.9%) and 6 hours (e.e. 11.3%).

EXAMPLE III

N-Benzylidene-R-tertiary-leucine amide (5.4 g, 24.8 mmol, e.e. 95.6%) and KOtBu (0.6 g, 4.96 mmol) were suspended in 50 ml of methylcyclohexane. The mixture was heated to reflux. The reaction mixture was analysed by chiral HPLC after 3 hours (e.e. 5.3%).

EXAMPLE IV

N-Benzylidene-R-tertiary-leucine amide (5.4 g, 24.8 mmol, e.e. 95.6%) and KOtBu (0.6 g, 4.96 mmol) were suspended in 25 ml of toluene. The mixture was heated to reflux. Samples were analysed by chiral HPLC after 1 hour (e.e. 3.4%) and 3 hours (e.e. 1.8%).

EXAMPLE V

N-Benzylidene-R-tertiary-leucine amide (5.4 g, 24.8 mmol, e.e. 95.6%) and KOtBu (0.6 g, 4.96 mmol) were suspended in 25 ml chlorobenzene. The mixture was heated to reflux. Samples were analysed by chiral HPLC after 1 hour (e.e. 11.3%) and 2 hours (e.e. 9.8%)

EXAMPLE VI

N-Benzylidene-R-tertiary-leucine amide (5.4 g, 24.8 mmol, e.e 95.6%) and KOtBu (0.6 g, 4.96 mmol) were suspended in 25 ml of anisole. The mixture was heated to reflux. Samples were analysed by chiral HPLC after 1 hour (e.e. 11.7%) and 3 hours (e.e. 10.0%)

EXAMPLE VII

N-Benzylidene-R-tertiary-leucine amide (5.4 g, 24.8 mmol, e.e. 95.6%) and a 20% solution of sodium ethoxide in ethanol (1.9 ml, 4.86 mmol) were suspended in 25 ml of toluene. The mixture was heated to reflux. Samples were analysed by chiral HPLC after 1 hour (e.e. 17.4%) and 3 hours (e.e. 4.6%).

EXAMPLE VIII

N-Benzylidene-R-tertiary-leucine amide (2.18 g, 10 mmol, e.e. 95.6%) was dissolved in 10 ml of toluene. A solution of 30% sodium methoxide in methanol (0.33 g, 2.5 mmol) was added. The mixture was heated to reflux and stirred for 7 hours and 20 minutes after which the e.e. had decreased to 3.5%.

COMPARATIVE EXPERIMENT 1

N-Benzylidene-R-tertiary-leucine amide (2.18 g, 10 mmol, ee 95% was dissolved in 10 ml of ethanol. A solution of potassium hydroxide in water (45%, 0.124 g, 1 mmol) was added. The mixture was heated to reflux. Samples were analysed by chiral HPLC after 1 hour (e.e. 93.4%) and 2 hours (e.e. 92.6%). The degree of racemisation was small.

COMPARATIVE EXPERIMENT 2

N-Benzylidene-R-tertiary-leucine amide (2.18 g, 10 mmol, e.e. 95%) was dissolved in 3 g of a 9:1 methanol/water mixture. A solution of potassium hydroxide in water (45%, 0.30 g, 2 mmol) was added. An extra quantity of 2.5 ml of the 9:1 methanol/water mixture was added, after which the mixture was heated to reflux. After 3 hours the e.e was still 95%, which indicated that no racemisation had taken place.

What is claimed is:

1. A process for racemising an enantiomer-enriched Schiff base of a primary amide of an amino acid which process comprises contacting said enantiomer-enriched Schiff base of a primary amide of an amino acid with a strong base in an organic solvent, wherein said strong base is chemically reactive with water.

2. The process of claim 1 wherein the strong base is a metal alkoxide, a metal alkyl, a metal amide, or a metal hydride.

3. The process of claim 2 wherein the strong base is a metal alkoxide.

4. The process of claim 1 wherein the strong base is present in an amount of 0.001–1000 mole % relative to the enantiomer-enriched Schiff base.

5. The process of claim 4 wherein the strong base is present in an amount of 0.1–100 mole % relative to the enantiomer-enriched Schiff base.

6. The process of claim 1 wherein the enantiomer-enriched Schiff base is an N-benzylidene primary amino acid amide.

7. The process of claim 1 wherein the enantiomer-enriched Schiff base is derived from an aliphatic primary amino acid amide.

8. The process of claim 7 wherein the enantiomer-enriched Schiff base is derived from tertiary-leucine amide.

9. The process of claim 1 wherein the organic solvent is an aromatic hydrocarbon, a cyclic aliphatic hydrocarbon or an ether.

10. The process of claim 9 wherein the organic solvent is an aromatic hydrocarbon.

11. The process of claim 1 wherein said enantiomer-enriched Schiff base has been prepared from the primary amide of the amino acid in said organic solvent.

* * * * *